(12) United States Patent
Catchpole et al.

(10) Patent No.: US 7,709,668 B2
(45) Date of Patent: May 4, 2010

(54) SEPARATION TECHNOLOGY

(75) Inventors: Owen John Catchpole, Wellington (NZ); Andrew Douglas Mackenzie, Wellington (NZ); John Bertram Grey, Wellington (NZ)

(73) Assignee: Industrial Research Limited, Lower Hutt (NZ)

( * ) Notice: Subject to any disclaimer, the term of this patent is extended or adjusted under 35 U.S.C. 154(b) by 0 days.

(21) Appl. No.: 10/512,221

(22) PCT Filed: Apr. 11, 2003

(86) PCT No.: PCT/NZ03/00062

§ 371 (c)(1),
(2), (4) Date: Jul. 13, 2005

(87) PCT Pub. No.: WO03/089399

PCT Pub. Date: Oct. 30, 2003

(65) Prior Publication Data

US 2006/0035350 A1    Feb. 16, 2006

(30) Foreign Application Priority Data

Apr. 22, 2002    (NZ) .................................... 518504

(51) Int. Cl.
*C07C 51/47* (2006.01)
(52) U.S. Cl. ...................... 554/186; 554/184; 554/185; 554/205
(58) Field of Classification Search ................. 435/134; 554/8, 186, 185, 184, 205
See application file for complete search history.

(56) References Cited

U.S. PATENT DOCUMENTS

| | | | |
|---|---|---|---|
| 5,502,077 A | 3/1996 | Breivik et al. | |
| 5,734,071 A | 3/1998 | Fex et al. ..................... | 554/186 |
| 6,528,669 B1 * | 3/2003 | Kulås et al. .................. | 554/186 |

FOREIGN PATENT DOCUMENTS

| | | |
|---|---|---|
| JP | 31-6634 | 1/1944 |
| JP | 60-214757 | 10/1985 |
| JP | 60214757 A * | 10/1985 |
| JP | 62-072793 | 4/1987 |
| JP | 02 025447 | 1/1990 |
| WO | WO95/11216 | 4/1995 |
| WO | WO01/10809 | 2/2001 |
| WO | WO 01/10809 | 2/2001 |
| WO | WO 01/36369 | 5/2001 |

OTHER PUBLICATIONS

Zhou et al. Enrichment of EPA and DHA from fish oil by urea inclusion-supercritical fluid. Zhejiang Gongye Daxue Xuebao (2000), 28 (4), 302-305.*
Derwent Abstract Accession No. 87-132623/19, JP 62-072793 A (Babcock-Hitachi KK), Sep. 26, 1985.
Patent Abstracts of Japan, JP 60-214757 A, (JGC Corp), Oct. 28, 1985.
Nilsson et al, JAOCS, vol. 65, No. 1, Jan 1988, pp. 109-117, Fractionation of Menhaden Oil Ethyl Esters Using Supercritical.
Shahidi et al, Trends in Food Sci & Tech 9, 1998, pp. 230-240, Omega-3 fatty acid concentrates: nutritional aspects and . . . .
Shahidi, Inform, vol. 13, Jan. 2002, Marine nutraceuticals.
Stansby, Fish Oils in Nutrition, Chapter 2, 1990, 289-308, Nutritional Properties of Fish Oil for Human Consumption . . . .
Stout et al, Fish Oils in Nutrition, Chapter 4, 1990, pp. 73-119, Fractionation of Fish Oils and their Fatty Acids.
Hayes et al, JAOCS, vol. 75, No. 10, 1998, pp. 1403-1409, Urea Complexation for the Rapid, Ecologically Responsible . . . .
Catchpole et al, J. Chem. Eng. Data 43, 1998, pp. 1091-1095, Solubility of Fish Oil Components in Supercritical $CO_2$ and $CO_2$ . . . .
Weber et al, Proc of 7th Meeting on Supercritical Fluids, 2000, pp. 71-76, A Closer Look at Gas Antisolvent Crystallisation.
Duck et al, J. of Korean Oil Chemists' Soc, vol. 14, No. 2, Aug. 1997, pp. 41-48, Separation of EPA and DHA from Fatty Acid . . . .
Nilsson et al, JAOCS, vol. 66, No. 11, Nov. 1989, Supercritical Fluid Fractionation of Fish Oil Esters Using Incremental . . . .
Hayes et al, Separation Sci and Tech 36(1), 2001, pp. 45-58, Triangular Phase Diagrams to Predict the Fractionation of . . . .
Liang et al, JAOCS, vol. 77, No. 7, 2000, pp. 773-777, Fraction-ation of Squid Visceral Oil Ethyl Esters by Short-Path . . . .
Luddy et al, J Amer Oil Chemists' Soc, vol. 37, Sep. 1960, pp. 447451, Direct Conversion of Lipid Components to Their Fatty . . . .
Malins et al, J Lipid Res 6, 1965, pp. 100-105, Composition of the diacyl glyceryl ethers and triglycerides of the flesh and . . . .
Johnathan P. Taylor, The selective extraction of squalene form the other components of deep-sea shark liver oils using (a) the crystallisation of urea complex, (b) liquid-liquid solvent extraction, [Online], 1998, Queensland, Australia, retrieved from Internet: URL:http://www.cheque.uq.edu.au/ugrad/theses/1998/pdf/JONT. PDF: retrieved on Aug. 27, 2008.
English Translation of Japanese Office Action dated Sep. 1, 2009.

* cited by examiner

*Primary Examiner*—Elvis O Price
(74) *Attorney, Agent, or Firm*—Jacobson Holman PLLC

(57) ABSTRACT

A process for extracting a wide range of lipophilic compounds from urea-containing solutions is described. The process utilises a near-critical fluid as the extraction solvent. The process is particularly applicable to the extraction of polyunsaturated fatty acids from the filtrate obtained upon urea fractionation, as employed in the processing of fish and other oils. In contrast to known processes, the lipophilic compounds may be extracted without the use of non-food grade solvents, and are suitable for pharmaceutical and cosmetic use.

39 Claims, 2 Drawing Sheets

SEPARATION TECHNOLOGY

This is a nationalization of PCT/NZ03/00062 filed Apr. 11, 2003 and published in English.

TECHNICAL FIELD

This invention relates to separation technology. A process, which employs a near-critical fluid, for extracting lipophilic compounds from urea-containing solutions is provided.

The process is particularly useful for extracting polyunsaturated fatty acids, or their derivatives, from the filtrate obtained following the urea fractionation of a mixture of fatty acids or their derivatives.

BACKGROUND ART

There is a substantial body of research which demonstrates the beneficial effects of polyunsaturated fatty acid (PUFA) consumption in the prevention and/or treatment of a variety of diseases including cardiovascular conditions, inflammatory diseases and some tumours [1, 2]. Therefore there is a demand for PUFA and their derivatives for use as, or in, dietary supplements and pharmaceuticals.

Separation of unsaturated fats and fat derivatives from saturated fats and fat derivatives is difficult because the unsaturated components are susceptible to thermal and oxidative degradation and because their physical properties do not differ from those of the saturated components [3]. The concentration of the unsaturated components in the form of parent triglycerides is more difficult, because the fatty acids are randomly arranged on the glycerol backbone of the triglyceride [3]. Therefore the parent oil is usually converted into free fatty acids (FFA) or fatty acid ethyl esters (FAEE) before separation into polyunsaturated and saturated fractions is carried out.

The use of urea complexes to separate saturated and monounsaturated fatty acids from polyunsaturated fatty acids has been known since the 1950's [3]. The stability of the complexes formed between urea and FFA is highly dependent on the degree of unsaturation in the fatty acids, with saturated fatty acids forming the most stable complexes and PUFA forming the least stable. The technique has been applied to the concentration of high value all cis-5,8,11,14,17-eicosapentaenoic acid (20:5ω3 or EPA) and all cis-4,7,10,13,16,19-docosahexaenoic acid (22:6ω3 or DHA) from fish oils [3], and to the extraction of γ-linolenic acid from seed oils [4].

The separation procedure is typically performed by dissolving a mixture of FFA (or fatty acid derivatives) in a hot aqueous alcohol solution that contains the appropriate amount of urea. When the solution is cooled, the urea preferentially forms solid complexes with saturated fatty acids and these are removed by filtration. The aqueous alcohol filtrate solution, which is enriched in unsaturated fatty acids, also contains urea. Therefore the fatty acids are recovered from the filtrate by solvent extraction with a non-polar organic solvent, such as hexane or isooctane, in which the urea is insoluble.

The use of non-food grade organic hydrocarbon solvents such as hexane in the extraction of PUFA or derivatives from the filtrate obtained following urea fractionation of a mixture of FFA or fatty acid derivatives is undesirable, particularly where the product is intended for use as a dietary supplement. Loss of the PUFA may occur during the reduction of the hydrocarbon solvent residues to regulatory levels.

Supercritical fluids are selective solvents that have found application in various extraction processes. A supercritical fluid has a density comparable to that of a liquid while exhibiting the diffusion properties of a gas. Thus, supercritical fluids have good solvent properties, which may be varied with pressure and temperature. Carbon dioxide is widely used as a supercritical fluid as its critical temperature and pressure (31° C., 74 bar) are attained relatively easily. Furthermore, $CO_2$ is inert, non-toxic, cheap and readily available.

Lipophilic compounds typically found in fish oil such as FFA, fatty acid esters, squalene, triglycerides, and glycerylethers are soluble to a certain extent in supercritical $CO_2$ [5]. Furthermore, their solubility increases at fixed temperature and pressure when ethanol is added to supercritical $CO_2$ [5]. Urea is almost insoluble in supercritical $CO_2$ and can be precipitated from ethanol solutions when they are admixed with supercritical $CO_2$ [6].

Known methods for employing supercritical fluids in combination with urea to separate PUFA or their derivatives from mixtures with other fatty acids or derivatives are batch-wise processes, with consequent low production rates. The use of supercritical fluid extraction after conventional urea fractionation to separate PUFA from other fatty acids requires the use of organic solvents.

WO01/10809 describes a batch-wise process in which polyunsaturated fatty acid ethyl esters can be recovered from solid complexes of mixed FAEE and urea using supercritical $CO_2$ at high pressures and relatively high temperatures, with the extent of recovery increasing with increasing temperature [7]. No application of this process to liquid feedstocks is described, and the applicants note that the use of co-solvents confers little or no advantage in the extraction of the esters. However, the specification does describe the use of ethanol as a co-solvent which, undesirably, caused urea to precipitate in the valves of the equipment.

In other systems, neat FFA or fatty acid derivatives are dissolved in supercritical $CO_2$ and the mixture contacted with solid urea that absorbs the saturated fatty acids or derivatives [3, 8, 9]. The capacity of the solid for saturated fatty acids is quickly reached, and the urea must be changed before the outlet composition of the extract in the process becomes the same as the original fatty acid material. An alternative method in which esters dissolved in supercritical $CO_2$ are mixed with a solution of urea in ethanol/water has also been described. Some of the esters are absorbed by the solution and form a solid complex with urea. This process has a low throughput, and requires long crystallisation times [3, 9].

Fatty acid esters have been fractionated in packed columns to produce PUFA concentrates using supercritical $CO_2$ after conventional urea crystallisation [10, 11]. However, this method of processing does not eliminate the need for organic hydrocarbon solvents or ensure that hydrocarbon solvent residues can be completely removed.

It is therefore an object of the present invention to provide a process for extracting a lipophilic compound from a solution containing urea, which goes some way towards overcoming the above disadvantages, or at least provides the public with a useful choice.

SUMMARY OF THE INVENTION

In a first aspect, the present invention provides a process for extracting a lipophilic compound from a solution including at least said lipophilic compound and urea, which process includes at least the steps of:
(a) contacting the solution with a near-critical fluid to produce a urea containing precipitate and a near-critical fluid phase containing the lipophilic compound;
(b) separating the near-critical fluid phase from the urea containing precipitate; and (c) reducing the pressure of the near-critical fluid phase to recover the lipophilic compound.

Lipophilic compounds amenable to extraction by a process of the invention include, but are not limited to, derivatives of triglycerides and glycerol ethers such as: fatty acids; fatty acid $C_1$-$C_4$ alcohol esters; fatty acid amines; fatty acid amides; alkoxyglycerol ethers; and fatty alcohols. In addition, non-glyceride lipophilic compounds such as fat soluble vitamins, sterols, wax esters, carotenoids and hydrocarbons (squalene, for example) are also amenable to extraction by a process of the invention.

Preferably, the fatty acid or derivative includes a chain of carbon atoms that is $C_{18}$ or longer.

Particularly preferred lipophilic compounds include polyunsaturated compounds such as: all cis-5,8,11,14,17-eicosapentaenoic acid (20:5ω3 or EPA); all cis-4,7,10,13,16,19-docosahexaenoic acid (22:6ω3 or DHA); 6,9,12-octadecatrienoic acid (γ-linolenic acid, or GLA); 9,12,15-octadecatrienoic acid (α-linolenic acid or ALA); 9,11-octadecadienoic acid (conjugated linoleic acid or CLA); squalene; vitamins A, D, and E and the esters thereof; and carotenoids (astaxanthin, β-carotene and lycopene, for example).

Preferably, the solution is a $C_1$-$C_4$ alcohol containing solution. More preferably, the solution is an ethanol containing solution.

Optionally, the solution is an aqueous alcohol containing solution and the urea containing precipitate is obtained as an aqueous solution.

Preferably, the solution is a filtrate obtained from the urea fractionation of a plurality of lipophilic compounds.

Preferably, the near-critical fluid is supercritical carbon dioxide.

The pressure of the near-critical fluid may be reduced in a single step but is preferably reduced in two or more steps to provide two or more fractions containing lipophilic compounds.

The extraction is desirably carried out as a continuous process wherein the urea containing precipitate and near-critical fluid phase are continuously removed from the extraction vessel without reducing the pressure of said vessel.

In a further aspect, the present invention provides a process for extracting at least one fatty acid from a lipid hydrolysate solution, which process includes at least the steps of:
(a) combining the hydrolysate solution with urea to produce a solid urea complex;
(b) separating the solid complex from the filtrate solution;
(c) contacting the filtrate solution with a near-critical fluid to produce a urea containing precipitate and a near-critical fluid phase containing the fatty acid;
(d) separating the near-critical fluid phase from the urea containing precipitate; and
(e) reducing the pressure of the near-critical fluid phase to recover the fatty acid.

In an alternative embodiment, the process of the invention is used to extract fatty acid esters from the solution obtained following the trans-esterification of a lipid with a suitable alcohol.

In a yet further aspect, the present invention provides a process for extracting a non-glyceride component from an oil solution, said oil solution comprising an oil dissolved in a suitable solvent or solvent mixture, which process includes at least the steps of:
(a) combining the oil solution with urea to produce a solid urea/lipophilic compound complex;
(b) separating the solid complex from the filtrate solution;
(c) contacting the filtrate solution with a near-critical fluid to produce a urea containing precipitate and a near-critical fluid phase containing the non-glyceride component;
(d) separating the near-critical fluid phase from the urea containing precipitate; and
(e) reducing the pressure of the near-critical fluid phase to recover the non-glyceride component.

The solid urea complex may be dissolved in an appropriate solvent mixture and the resulting solution subjected to a process of the invention to extract free fatty acids. Advantageously, the urea obtained from the extraction of the urea complex may be recycled and used to treat further lipid hydrolysate in a process of the invention.

In a still further aspect the present invention provides a process further comprising extracting a lipophilic compound which process includes at least the steps of:
(f) dissolving the solid urea/lipophilic compound complex in a suitable solvent or solvent mixture to form a solution;
(g) contacting the solution with a near-critical fluid to produce a urea containing precipitate and a near-critical fluid phase containing at least one lipophilic compound;
(h) separating the near-critical fluid phase from the urea containing precipitate; and
(i) reducing the pressure of the near-critical fluid phase to recover the lipophilic compound.

In another aspect the present invention provides a lipophilic compound or plurality of lipophilic compounds when extracted by a process of the invention.

Although the present invention is broadly as defined above, those persons skilled in the art will appreciate that the invention is not limited to it and that the invention also includes embodiments of which the following description gives examples.

DETAILED DESCRIPTION OF THE INVENTION

Figure 1:
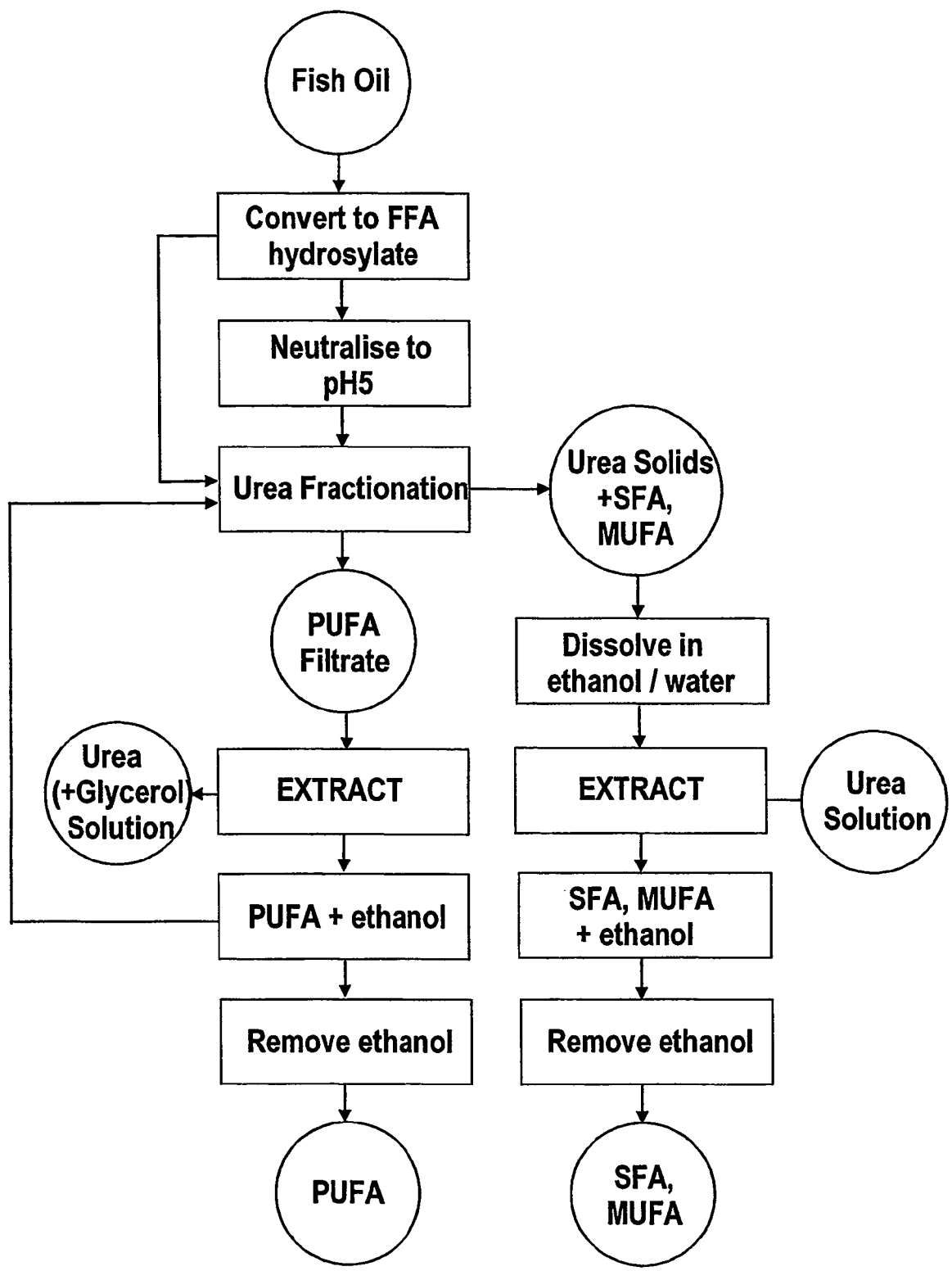
FIG. 1 is a simple flow diagram showing a process for the extraction of polyunsaturated fatty acids (PUFA) from fish oil.

The present invention is broadly directed to the separation of mixtures of lipophilic compounds.

Accordingly, in a first aspect, the present invention provides a process for extracting a lipophilic compound from a solution including at least said lipophilic compound and urea, which process includes at least the steps of:
(a) contacting the solution with a near-critical fluid to produce a urea containing precipitate and a near-critical fluid phase containing the lipophilic compound;
(b) separating the near-critical fluid phase from the urea containing precipitate; and
(c) reducing the pressure of the near-critical fluid phase to recover the lipophilic compound.

The term "contact" as used herein generally means admixing the solution with the near-critical fluid in suitable apparatus connected to or contained within an extraction vessel/precipitation chamber as are well known in the art. Suitable apparatus includes, but is not limited to: a static mixer; a nozzle; a mixing valve; packing (structured or random); a tee-joint; membrane contactor, and concentric pipes.

Preferably, the solution and near-critical fluid are contacted using a static mixer.

The term "separate" as used herein generally means removing the stream comprising the near-critical fluid phase and the dissolved lipophilic compound from the apparatus, while excluding the precipitated urea from the stream.

The term "near-critical fluid" as used herein means a fluid that is close to its critical point and thus includes both sub-critical and supercritical fluids. Near-critical includes the reduced temperature range $0.75 \leq T_r \leq 1.25$ (where $T_r$ is the temperature divided by the critical temperature, $T_c$ of the fluid); and the pressure ranges $P > P_v$ (where $P_v$ is the vapour pressure) for $T < T_c$ and $P > P_c$ (where $P_c$ is the critical pressure) for $T \geq T_c$.

Preferably, the near-critical fluid used is supercritical $CO_2$. The supercritical $CO_2$ may be admixed with the filtrate solution at a desired pressure ($\geq 75$ bar) and desired temperature, $T$ ($>31.2°$ C.). Alternatively, liquid $CO_2$ can be used ($T<31.2°$ C., pressure greater than the vapour pressure of $CO_2$ at T); or other near-critical gases that are known in the art such as: ethane; ethylene; propane; propylene; butane; fluorinated $C_2$-$C_3$ hydrocarbons, particularly R134a (1,1,1,2-tetrafluoroethane); nitrous oxide; sulfur hexafluoride; dimethylether; partially and fully fluorinated analogues of dimethylether; and mixtures of any two or more of the above gases.

Preferably, the temperature is in the range 273-353 K, and the pressure is sufficient to ensure complete extraction of the lipophilic compound.

In a particularly preferred embodiment, the near-critical fluid is supercritical $CO_2$, the temperature is in the range 308-353 K, and the pressure is in the range 150-500 bar. More preferably, the pressure is in the range 150-300 bar.

Suitable lipophilic compounds are those which are soluble in the near-critical fluid, or are soluble in a mixture of the near-critical fluid and one or more $C_1$-$C_4$ alcohols.

Lipophilic compounds amenable to extraction by a process of the invention include, but are not limited to, derivatives of triglycerides and glycerol ethers such as: fatty acids; fatty acid $C_1$-$C_4$ alcohol esters; fatty acid amines; fatty acid amides; alkoxyglycerol ethers; and fatty alcohols. In addition, non-glyceride lipophilic compounds such as fat soluble vitamins, sterols, wax esters, carotenoids and hydrocarbons (squalene, for example) are also amenable to extraction by a process of the invention.

It will be appreciated that any lipophilic compounds that are not soluble in the near-critical fluid (hydrolysed phospholipid derivatives, for example) will co-precipitate with the urea.

In addition, other compounds that are not soluble in the near-critical fluid, such as chlorophyll derivatives, will co-precipitate with the urea. Therefore, the process of the invention may be applied to at least partially decolourise lipophilic compounds.

Preferably, the fatty acid or derivative includes a chain of carbon atoms which is $C_{18}$ or longer.

Particularly preferred lipophilic compounds include polyunsaturated compounds such as: all cis-5,8,11,14,17-eicosapentaenoic acid (20:5ω3 or EPA); all cis-4,7,10,13,16,19-docosahexaenoic acid (22:6ω3 or DHA); 6,9,12-octadecatrienoic acid (γ-linolenic acid, or GLA); 9,12,15-octadecatrienoic acid (α-linolenic acid or ALA); 9,11-octadecadienoic acid (conjugated linoleic acid or CLA); squalene; vitamins A, D, and E and the esters thereof; and carotenoids (astaxanthin, β-carotene and lycopene, for example).

Preferably, the solution is a $C_1$-$C_4$ alcohol containing solution. More preferably, the solution is an ethanol containing solution.

Optionally, the solution is an aqueous solution, and the urea co-precipitates with water to form a liquid phase. Advantageously, said liquid phase may be continuously removed from the extraction vessel under pressure.

Preferably, the solution is an aqueous alcohol solution and is a filtrate obtained from the urea fractionation of a plurality of lipophilic compounds.

As discussed above, urea preferentially forms solid complexes with saturated lipophilic compounds, for example free fatty acids (FFA). The urea fractionation process is generally carried out by adding a mixture of FFA to a hot aqueous alcohol solution of urea. The alcohol used is generally methanol or ethanol but is not limited thereto. Upon cooling, solid urea complexes form and these may be filtered to give a filtrate enriched in unsaturated fatty acids.

The relative concentrations of alcohol and water influence the degree to which FFA or their derivatives are complexed by urea. The ratio of urea to FFA, and the final temperature to which the solution is cooled, also affect the degree of complexation [3, 4, 12].

The effects of: water content (relative concentrations of ethanol or methanol to water); temperature; urea to FFA ratio; and urea to solvent ratio on the separation of FFA have been quantified by Hayes et al. [4, 12]. Increasing the water content of the solvent above 10% by mass causes a sharp reduction in the removal of saturated fatty acids and monounsaturated fatty acid by complex formation with urea [4, 12]. Increasing the water content substantially reduces the solubility of fatty acid esters, and to a lesser extent, FFA. However, an increase in the water content enables an easier separation of the urea and FFA after dissociation of the complex by heating [13]. Increasing the water content increases the solubility of urea, and so an optimum may be reached to balance the inverse solubilities of FFA and urea.

The ratio of urea to FFA determines the loss of high value polyunsaturated fatty acids (PUFA). At high urea to FFA ratios, the complex formation process becomes indiscriminate, and large losses of PUFA occur, although all saturates and most monounsaturates are also complexed [4, 12]. As the ratio decreases, the process becomes more selective for firstly saturates, and then monounsaturates [4, 12]. At low ratios, only saturates are complexed, and the process must be repeated many times to achieve the desired level of separation.

Similarly, the temperature at which the crystallisation takes place influences the extent of complexation of saturated fatty acids (SFA), monounsaturated fatty acids (MUFA), PUFA and, if present, alkoxyglyceryl ethers (AGE) or fatty alcohols. The lower the temperature, the lower the solubility of urea in the solvent solution, and the higher the degree of complexation of all FFA species [3].

In an alternative embodiment, the urea fractionation process is carried out by passing an alcohol, or aqueous alcohol, solution of FFA or fatty acid derivatives through a packed bed or column of finely ground solid urea. The alcohol used is generally methanol or ethanol but is not limited thereto. Generally, the process is performed at a temperature where SFA or derivatives form a solid complex with the urea. Preferably, the process is performed at a temperature where MUFA or derivatives form a solid complex with the urea. The solution is separated from the solid material by percolation, filtration, or other suitable means, to give a filtrate which contains dissolved urea and is enriched in unsaturated fatty acids.

The optimum conditions for the separation of PUFA from a mixture that also contains SFA and/or MUFA can be determined through routine experimentation.

In one embodiment, the process of the invention is used to extract FFA from an aqueous ethanol solution obtained following the urea fractionation of a mixture of FFA.

Preferably, the concentration of water in said solution is between 5% and 30% by volume. More preferably, the concentration of water is between 10% and 20% by volume.

In an alternative embodiment the process of the invention is used to extract fatty acid esters (FAE) from an aqueous ethanol solution obtained following the urea fractionation of a mixture of FAE. As discussed above, FAE are generally less soluble in ethanol/water mixtures than are FFA. The determination of the appropriate ethanol/water ratio for use in such a process is within the ability of those persons skilled in the art.

Preferably, the concentration of water in said solution is between 5% and 20% by volume. More preferably, the concentration of water is between 5% and 10% by volume The process of the invention is particularly suited to the extraction of FFA or fatty acid derivatives from the filtrate obtained following the urea fractionation of oils or fats obtained from animal or plant sources. Such oils and fats include, but are not limited to: oils obtained from marine organisms (especially fish, shellfish and seaweed); animal fats such as butter, lanolin or lard; vegetable oils (including oils derived from the purification of vegetable oils such as olive oil deodoriser distillate and soya oil deodoriser distillate); complex lipids (especially phospholipids and sphingolipids); seed oils (especially borage, evening primrose, blackcurrant, *Echium, Lunarium,* meadowfoam, saw palmetto, pumpkin and *Biota orientalis*); and nut oils.

The process of the invention is especially suited to the extraction of PUFA from fish oils, shellfish oils and seed oils, and to the extraction of conjugated PUFA from animal fats.

Accordingly, in one embodiment, supercritical $CO_2$ is introduced into an extraction vessel together with the aqueous ethanol filtrate solution obtained following the urea fractionation of a suitably pre-processed oil or fat.

Preferably, the oil or fat is fish oil or seed oil.

Suitable pre-processing generally means that the oil, complex lipid or fat has been processed to remove protein residues. In addition, prior to undergoing urea fractionation, the oil, complex lipid or fat is generally hydrolysed to yield FFA, trans-esterified with ethanol to give FAEE, or converted to other derivatives discussed above.

It will be appreciated that oils already enriched in FFA (such as olive oil deodoriser distillate, soya oil deodoriser distillate, and saw palmetto oil) may be subjected to urea fractionation without hydrolysis, transesterification or conversion to other derivatives. Accordingly, such oils may undergo urea fractionation directly after dissolution in a suitable solvent or solvent mixture, such as ethanol or aqueous ethanol.

The $CO_2$ simultaneously reduces the pH of the filtrate solution, and extracts the FFA or fatty acid derivatives, and most of the ethanol. Ethanol acts as a co-solvent, which greatly increases the solubility of the FFA. Urea and water are precipitated into the extraction vessel, and can be continuously removed as a liquid solution of urea in water.

The $CO_2$ solution of FFA or fatty acid derivatives is transferred to a suitable vessel where the pressure is reduced to the point where ethanol and FFA are precipitated into the vessel as a liquid stream.

The pressure reduction can be carried out in one step or multiple steps, to give more than one fraction of FFA. FFA may then be recovered from the liquid stream(s) by evaporation of ethanol.

Generally, as the pressure is reduced, those fatty acids or derivatives that are least soluble in the near-critical fluid will precipitate first. The most soluble fatty acids or derivatives will precipitate last. Therefore it will be appreciated that a degree of separation or fractionation of the fatty acids or derivatives from one another may be achieved.

The fractionation is related to molecular mass and to a much lesser extent degree of unsaturation, as high molecular mass, highly unsaturated fatty acids or derivatives are generally less soluble than are lower molecular mass compounds. Lipophilic compounds of similar molecular mass but different polarity such as AGE and FFA or FAEE may also be fractionated according to the difference in polarity.

Alternatively, or in addition to fractionation by step-wise pressure reduction, the FFA may be further fractionated in a packed column.

Advantageously, the FFA and ethanol solutions resulting from the separation steps(s) may be subjected to an additional urea fractionation step, without having to evaporate the ethanol, to increase the relative PUFA content.

Optionally, a high-pressure water wash column is introduced after the extraction step, and before the pressure reduction steps, to remove urea that is extracted by near-critical $CO_2$ and ethanol. This is particularly useful when dilute solutions of PUFA ethyl esters in a mostly ethanol solution are obtained as the filtrate from urea fractionation because, as discussed above, the solubility of urea increases with increasing ethanol concentration. Similarly, an additional water stream may be injected along with the filtrate at the point of contact with $CO_2$ to improve the precipitation of urea.

In a further aspect, the present invention provides a process for extracting at least one fatty acid from a lipid hydrolysate solution, which process includes at least the steps of:
(a) combining the hydrolysate solution with urea to produce a solid urea/lipophilic compound complex;
(b) separating the solid complex from the filtrate solution;
(c) contacting the filtrate solution with a near-critical fluid to produce a urea containing precipitate and a near-critical fluid phase containing the fatty acid;
(d) separating the near-critical fluid phase from the urea containing precipitate; and
(e) reducing the pressure of the near-critical fluid phase to recover the fatty acid.

The urea may be added to the lipid hydrolysate solution as a solid. However, this may require the hydrolysate solution being held above ambient temperature in order to dissolve the urea, which may result in degradation of PUFA. Accordingly, the hydrolysate solution will generally be combined with a solution of urea.

In an alternative embodiment, the lipid hydrolysate solution is added to finely ground solid urea which is in the form of a column or packed bed. Generally, the process is performed at a temperature where SFA or derivatives form a solid complex with the urea. Preferably, the process is performed at a temperature where MUFA or derivatives form a solid complex with the urea. The lipid hydrolysate solution is passed through the column or bed to give a filtrate which is separated from the solid material by percolation, filtration, or other suitable means.

It will be appreciated that the solid urea complex will generally be enriched in saturated fatty acids while the filtrate will generally be enriched in unsaturated fatty acids.

The lipid hydrolysate solution will generally be obtained by the alkaline hydrolysis of a suitable fat, complex lipid, oil, or mixture thereof.

Optionally, the lipid hydrolysate solution is winterised prior to being combined with urea. The hydrolysate solution is cooled to a temperature in the range between −20° C. and 10° C., precipitating some components of the lipid hydrolysate solution, for example SFA, sterols, waxes and fat soluble vitamins. Advantageously, the precipitated material may be removed from the lipid hydrolysate solution by filtration or other suitable means.

In one embodiment, the lipid hydrolysate solution is obtained from the hydrolysis of fish, animal or plant oil containing both triglycerides and wax esters. Therefore, in this embodiment, the lipid hydrolysate solution contains FFA and fatty alcohols.

In a further preferred embodiment, the lipid hydrolysate solution is obtained from the hydrolysis of fish oil containing both triglycerides and diacylglyceryl ethers, and optionally squalene. Therefore, in this embodiment, the lipid hydrolysate solution contains FFA and alkoxyglyceryl ethers, and optionally squalene.

In a particularly preferred embodiment, the lipid hydrolysate solution is obtained from the hydrolysis of fish oil containing triglycerides rich in DHA and EPA. Therefore, in this embodiment, the lipid hydrolysate solution substantially comprises FFA, some of which is EPA and DHA.

In another preferred embodiment, the lipid hydrolysate solution is obtained from the hydrolysis of seed oil containing triglycerides rich in GLA and optionally ALA. Therefore, in this embodiment, the lipid hydrolysate solution substantially comprises FFA, some of which is GLA, and optionally ALA.

Lipid hydrolysate solutions will generally have a high pH and also contain glycerol and alkali salts.

When such solutions are subject to a process of the invention using near-critical $CO_2$, glycerol will also precipitate into the aqueous rich phase, as will alkali carbonates that form due to reaction with $CO_2$. Advantageously, the pH of the solution is reduced such that FFA are extracted into the near-critical fluid and the substantially aqueous liquid phase may be removed continuously from the extraction vessel without reducing the pressure of the extraction vessel.

In an alternative embodiment, the process of the invention is used to extract fatty acid esters from the solution obtained following the trans-esterification of a lipid with a suitable alcohol.

Preferably, the lipid is trans-esterified with a $C_1$-$C_4$ alcohol, more preferably ethanol.

It will be appreciated that the process of the invention may also be applied to the extraction of non-glyceride components from the solution obtained following the dissolution of an oil already rich in FFA in a suitable solvent or solvent mixture.

Accordingly, in an alternative embodiment, the present invention provides a process for extracting a non-glyceride component from an oil solution, said oil solution comprising an oil dissolved in a suitable solvent or solvent mixture, which process includes at least the steps of:
(a) combining the oil solution with urea to produce a solid urea/lipophilic compound complex;
(b) separating the solid complex from the filtrate solution;
(c) contacting the filtrate solution with a near-critical fluid to produce a urea containing precipitate and a near-critical fluid phase containing the non-glyceride component;
(d) separating the near-critical fluid phase from the urea containing precipitate; and
(e) reducing the pressure of the near-critical fluid phase to recover the non-glyceride component.

Preferably, the non-glyceride component is selected from the group consisting of: squalene; vitamin E; and carotenoids.

Preferably the oil is selected from the group consisting of: olive oil deodoriser distillate; soya oil deodoriser distillate; and saw palmetto oil.

Preferably, the oil solution is an ethanol or aqueous ethanol solution.

Optionally, the solution is winterised before being combined with urea.

The process of the invention is also applicable to the extraction of lipophilic compounds, for example SFA, MUFA (especially oleic acid), and alkoxyglycerylethers, from the solid urea complex obtained during urea fractionation. If the urea complex is dissolved in suitable solvent mixture at a sufficiently high temperature, the complex will dissociate. The solvent mixture may then be contacted with a near-critical fluid in a process of the invention to precipitate the urea and recover the lipophilic compounds, which in turn may be fractionated in two or more steps. Advantageously, the urea may be recovered and reused in a subsequent fractionation process.

Accordingly, in one embodiment the process of the invention further comprises extracting a lipophilic compound said process including at least the steps of:
(f) dissolving the solid urea/lipophilic compound complex in a suitable solvent or solvent mixture to form a solution;
(g) contacting the solution with a near-critical fluid to produce a urea containing precipitate and a near-critical fluid phase containing at least one lipophilic compound;
(h) separating the near-critical fluid phase from the urea containing precipitate; and
(i) reducing the pressure of the near-critical fluid phase to recover the lipophilic compound.

Preferably, the solvent or solvent mixture contains a $C_1$-$C_4$ alcohol. More preferably, the solvent or solvent mixture contains ethanol.

Preferably, the solvent or solvent mixture is aqueous alcohol.

In a preferred embodiment the lipophilic compound is oleic acid.

The invention may be better understood with reference to FIG. 1, which is a simple flow diagram showing a process, for the extraction of polyunsaturated fatty acids (PUFA) from fish oil, which incorporates the invention. In the process represented in this diagram, an aqueous ethanolic solution of fish oil is hydrolysed to give a lipid hydrolysate solution which contains FFA. The hydrolysate solution is optionally neutralised to a pH between about 5 and about 7 by the addition of acid.

A process of the invention is then applied in which:
(1) the hydrolysate solution is combined with urea;
(2) the resulting mixture is filtered to give a filtrate containing PUFA and a solid comprising urea, SFA and MUFA;
(3) the filtrate is contacted with a near-critical fluid to give a product stream which is an aqueous solution of glycerol and urea and a near-critical fluid phase comprising PUFA and ethanol;
(4) the near-critical fluid phase is separated from the aqueous solution; and
(5) the pressure of the near-critical fluid phase is reduced to give another product stream which is an ethanolic solution of PUFA.

Steps (3) to (5) are what is meant by "EXTRACT".

The ethanolic solution of PUFA may be subjected to another urea fractionation and near-critical fluid extraction to further increase the concentration of PUFA. Alternatively, the ethanol may be evaporated to give the PUFA.

The urea containing solid enriched in SFA and MUFA is dissolved in aqueous ethanol and a process of the invention applied in which:
(1) the solution is contacted with a near-critical fluid to give a product stream which is an aqueous solution of urea and a near-critical fluid phase comprising SFA, MUFA and ethanol;

(2) the near-critical fluid phase is separated from the aqueous solution; and (3) the pressure of the near-critical fluid phase is reduced to give another product stream which is an ethanolic solution of SFA and MUFA.

It will be appreciated that the term "EXTRACT" may also be applied to Steps (1) to (3).

Evaporation of the ethanol from the ethanolic solution of SFA and MUFA gives SFA and MUFA.

Thus the fatty acids; PUFA, MUFA and SFA; may be extracted from the fish oil without using any hydrocarbon solvents.

In a further aspect the present invention provides a lipophilic compound or plurality of lipophilic compounds when extracted by a process of the invention.

Using a process of the invention the lipophilic compounds may be obtained free of non-food grade solvent residues. Such lipophilic compounds are therefore suitable for use in or as dietary supplements or in the formulation of pharmaceuticals and cosmetics.

EXPERIMENTAL

Apparatus

Figure 2:
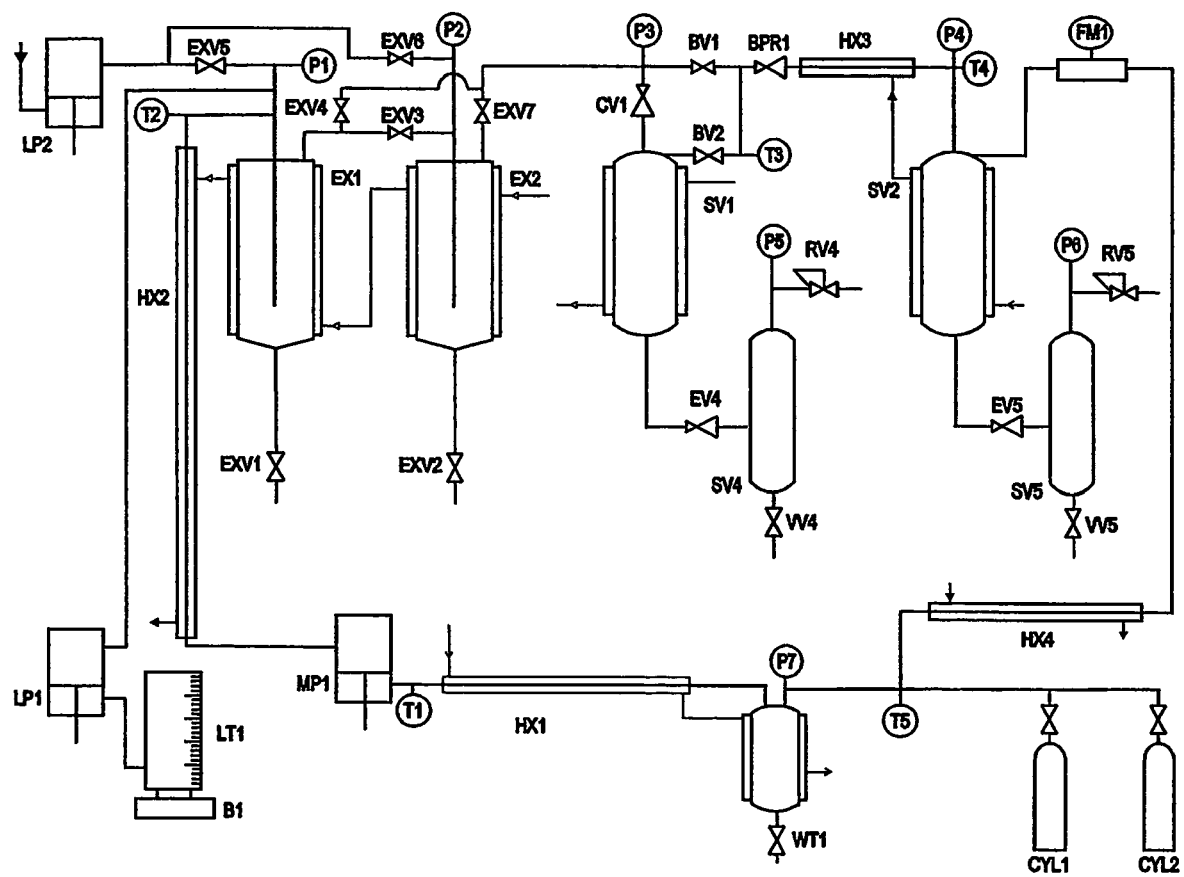
FIG. 2 is a schematic diagram of an extraction apparatus with a capacity of 10 liters, which is suitable for use in performing an extraction process of the invention.

Experiments were carried out in the pilot scale 10 liter apparatus shown in FIG. 2.

General Procedure and Methods for 10 Litre Apparatus Experiments

The 10 liter apparatus is shown in, and described with reference to, FIG. 2. $CO_2$ (or other near-critical solvent) was supplied to the apparatus by liquid supply cylinders CYL1 and CYL2. The $CO_2$ then passed through a chilled water trap WT1 and condenser/subcooler HX1 before being compressed to the operating pressure by a positive displacement pump MP1. The compressed $CO_2$ then passed through preheater heat exchanger HX2, and then into the extraction vessel EX1 via a vertical downcomer tube, or downcomer tube and static mixer.

Simultaneously, solution containing urea and fat derivatives (acids or ethyl esters), water and ethanol was withdrawn from a supply tank LT1 mounted on a balance B1, and was then compressed to the operating pressure by piston pump LP1. The high pressure solution was then mixed with the $CO_2$ in a tee joint just prior to the downcomer tube/static mixer that passed into EX1. Urea and water was precipitated, and recovered at regular time intervals from the base of EX1 via valve EXV1 without reducing the pressure in EX1. The fat derivatives and ethanol were dissolved in the $CO_2$, and left the extraction vessel via an outlet near the top of the vessel.

The combined $CO_2$ rich solution then passed through valve EXV4 (to bypass vessel EX2, valves EXV3 and EXV7 are shut), a pressure reduction valve CV1, where the pressure was reduced to 90-120 bar, and then into jacketed separation vessel SV1. Part of the extract and a small amount of ethanol were precipitated into this vessel. This extract was recovered at regular time intervals by further depressurisation through valve ER4 into an additional separator held at 30 bar, and then through valve VV4. Ethanol was removed from the extract by evaporation under vacuum. The resultant PUFA was washed with hot water to remove any co-extracted urea.

$CO_2$ resulting from flashing of the ethanol at 30 bar was vented to the atmosphere via a relief valve RV4. The bulk of the $CO_2$ and extract exited the top of SV1 and then passed through a back pressure regulator BPR1, where the pressure was reduced to cylinder pressure (50-60 bar), before entering the second separation vessel SV2 via heat exchanger HX3. The remainder of the extract and ethanol was precipitated into this vessel. This extract was recovered at regular time intervals by further depressurisation through valve EV5 to 30 bar into vessel SV5, and then through valve VV5. Ethanol was removed from the extract by evaporation under vacuum. The resultant PUFA was washed with hot water to remove any co-extracted urea.

$CO_2$ resulting from flashing of the ethanol at 30 bar was vented to the atmosphere via relief valve RV5. The bulk of the $CO_2$ exited the top of SV2 and then passed through a coriolis mass flow meter FM1, cooler heat exchanger HX4 before being recycled back to MP1 via the water trap WT1.

The additional water-wash vessel EX2 was used for Examples 7 and 8. EX2 was inserted into the flow path between extraction vessel EX1 and separator SV1. Valves EXV3 and EXV7 were open to enable $CO_2$ flow through vessels EX1 and EX2 sequentially, and valve EXV4 was closed. A high pressure pump LP2, identical to LP1, was used to pump water into vessel EX2. The wash column EX2 is substantially identical in dimension and operation to extraction vessel EX1. The high pressure solution ($CO_2$ and dissolved extract) from EX1 was mixed with the water from pump LP2 in a tee joint just prior to the downcomer tube/static mixer that passed into EX2. Co-extracted urea from EX1 and water from LP2 was precipitated, and recovered at regular time intervals from the base of EX2 via a valve EXV2 (as described above for EX1). The fat derivatives and some ethanol remained dissolved in the $CO_2$, and left the extraction vessel EX2 via an outlet near the top of the vessel. The combined $CO_2$ rich solution then passed through pressure reduction valve CV1 as described above for standard operation. Ethanol was removed from extract samples obtained from SV1 and SV2 by evaporation under vacuum. The samples did not require washing with water as all urea had been removed in the water-wash step.

Materials and Methods

Industrial grade liquid carbon dioxide was supplied by BOC (New Zealand) Ltd. Ling and dogfish liver oils were supplied by MacCure Seafoods Ltd (Nelson, New Zealand). Industrial grade urea was supplied by Petrochem NZ Ltd. All other chemicals used in the synthesis of fatty acids or ethyl esters were laboratory grade.

Production of Free Fatty Acids from Fish Oil

Free fatty acids (FFA) were prepared by reacting 1 kg of fish oil with 5 L of 1 M KOH (in 90% ethanol) overnight at room temperature under nitrogen in the dark with gentle stirring.

Urea Fractionation of Fish Oil FFA

The solution of hydrolysed fish oil in ethanol was neutralised by the slow addition of 6 N HCl (typically approximately 450 mL of acid was required). Urea (1.5 kg) was dissolved in 90% ethanol (5 L) at 65° C. in a 20 L glass vessel. The fish oil FFA solution (preheated to 60° C.) was added slowly to the urea solution, and the mixture left at room temperature for 1 hr. The mixture was then cooled to 4° C. or −20° C. and left overnight after which the mixture was vacuum filtered through Whatman #1 filter paper.

A second fractionation of hydrolysed fish oil (Ling and Spiny Dogfish) was conducted on FFA/ethanol mixtures obtained from the Examples. The mixtures measured approximately 4 L of which 350 g was FFA (Ling) and approximately 7.5 L of which 550 g was FFA and alkoxyglyceryl ethers (AGE) (Dogfish). They were added to urea solutions (1 kg of urea in 4 L of 90% ethanol at 65° C.; and 1.8 kg of urea in 7.5 L of 90% ethanol at 65° C. respectively) and the resulting mixtures cooled to −20° C. For each fractionation, a sample (10 ml) of the total collected filtrate was extracted into petroleum ether to determine the FFA (and AGE) content of the liquid. Similarly, for each fractionation, a sample (10 g) of the total crystals was also extracted into petroleum ether to determine the FFA and AGE content of the solid. These extracts were analysed by gas chromatography (GC) in order to determine the percentage of saturated (SFA), monounsaturated (MUFA) and polyunsaturated (PUFA) fatty acids and AGE in the extracts.

Production of Fatty Acid Ethyl Esters (FAEE) from Fish Oil

FAEE were prepared by reacting 1 kg of fish oil with 1.33 L of 0.5 M sodium ethoxide/ethanol solution for 3 hours at room temperature under nitrogen in the dark with gentle stirring [14]. Distilled water (250 ml) was added to quench the reaction. Dilute HCl (2N, 125 ml) was added and the mixture separated into two phases. The lower layer containing glycerol and salts was discarded. The upper layer was washed with distilled water (500 ml) and the lower layer again discarded. The upper layer containing fatty acid ethyl esters and, for dogfish oil samples, glyceryl ethers was then collected. The complete conversion of fish oil triglycerides into FAEE was confirmed by thin layer chromatography (TLC).

Urea Fractionation of Fish Oil FAEE

Urea (1.5 kg) was dissolved in 90% ethanol (6 L) at 65° C. in a 10 L screwtop bottle. FAEE (500 g) dissolved in ethanol (500 ml) and preheated to 60° C. were added slowly to the urea solution. Crystals formed instantly and the mixture was removed from the water bath and placed at room temperature for 1 hour. The mixture was then refrigerated (4° C.) or left at room temperature overnight after which the mixture was vacuum filtered through Whatman #1 filter paper. A sample (10 ml) of the total collected filtrate (6.5 L) was extracted into petroleum ether to determine the FAEE content of the liquid (151 g). A sample (10 g) of the total crystals (1.9 kg) was also extracted into petroleum ether to determine the FAEE content of the solid. These extracts were analysed by GC in order to determine the percentage of SFA, MUFA and PUFA in the extracts.

Analysis of Fatty Acids, Ethyl Esters, Glyceryl Ethers

TLC Analysis of Lipid Classes

Lipid samples were dissolved in petroleum ether (30-40 mg/ml) and spotted onto silica gel plates (Merck, 60 $F_{254}$). Non-polar lipid classes were analysed by running the plates with a petroleum ether:diethyl ether:acetic acid (80:20:1) solvent mixture. The plates were then dipped in a solution of sulfuric acid (2% in ethanol) and the spots developed by charring with a heat gun.

GC Analysis of Fatty Acid Composition

The FFA or fish oils were converted to fatty acid methyl esters (FAME) before analysis [15]. Oil (20 mg) was dissolved in hexane (0.5 ml, containing 1 mg nonadecanoic acid internal standard) and added to 1% $H_2SO_4$ in methanol in a sealed test tube. The test tube was placed in a water bath at 50° C. overnight. Hexane (2 ml) and 5% sodium chloride solution (2 ml) were added to the mixture and the organic layer (which contained the FAME) was removed. The organic layer was then washed with 2% sodium bicarbonate solution (2 ml).

Glyceryl ethers were derivatised for GC analysis by acetonation [16]. Hydrolysed dogfish oil (20 mg) was added to acetone (5 ml) and 2 drops of perchloric acid and allowed to stand for 30 min. Water (3 ml) was added to quench the reaction, and mixture basified by the addition of ethanolic KOH (1 M, 1 ml). The isopropylidene derivatives of glyceryl ethers were extracted into petroleum ether (2×3 ml) and analysed by GC. The aqueous phase was then acidified (1 mL of 2N HCl) and the FFA extracted into petroleum ether (2×3 ml) and converted to FAME for GC analysis.

FAEE were simply dissolved in petroleum ether (10 mg/ml) for analysis. GC analysis was carried out using a Hewlett-Packard 5890 GC equipped with an EC-Wax (Altech) column (30 m×0.25 mm×0.25 μm) with an inlet pressure of 10 PSI. The oven temperature was held at 165° C. for 3 min then heated at 4° C./min to 195° C. and held for 10 min. The temperature was then raised at 4° C./min to 225° C. with a final holding time of 12 min. FAEE were detected using a flame ionisation detector (FID). Peaks were identified by comparison of retention times with those of fatty acid standards and fatty acids contained in previously well-characterised natural oils (e.g. cod liver oil).

EXAMPLE 1

Separation of Urea, Glycerol, Salts and FFA

This example demonstrates the process for recovering FFA from the conversion of fish oil triglycerides to FFA followed directly by urea complexation.

Ling liver oil (1 kg) containing 10.8% DHA and 24.0% PUFA was hydrolysed in ethanol/water (90:10 mass ratio) using potassium hydroxide. The pH of the final solution was approximately 14. A saturated urea solution was prepared by mixing 1 kg of urea into 3 L of 90% by mass ethanol/water and then heating to 60° C. This solution was then mixed with the fatty acid hydrolysate solution and allowed to slowly cool. The total solution was then placed in a freezer overnight, and then removed the next day and filtered under gravity to separate the solid urea complex from the filtrate. 6.74 kg of the filtrate was then pumped at 200 bar, at an average mass flow rate of 1.80 kg per hour. The filtrate was mixed with supercritical $CO_2$ at 200 bar and 40° C. before entering the precipitation chamber. The supercritical carbon dioxide was pumped at the rate of approximately 12.3 kg per hour. A precipitate of mainly water, urea, glycerol and phospholipid derivatives was obtained from the bottom of the precipitation chamber at a rate of approximately 0.61 kg per hour. The supercritical carbon dioxide and dissolved ethanol and FFA passed through two separation stages by sequential pressure reduction. The separators were held at approximately 110 bar and 60 bar respectively.

The first separation stage yielded an extract containing mainly $C_{18}$-$C_{22}$ MUFA and PUFA, and some ethanol at an average rate of 0.15 kg per hour. A total of 70 g of FFA were recovered in this fraction after evaporation of the ethanol, with a all cis-4,7,10,13,16,19-docosahexaenoic acid (DHA) content of 22.7%; and PUFA content of 40.8% by mass.

The second separation stage yielded a second extract fraction containing mostly $C_{16}$-$C_{22}$ MUFA and PUFA, and ethanol at an average rate of 0.97 kg per hour. A total of 293 g of FFA was obtained from this fraction (after evaporation of the ethanol from a sample of known mass), with a DHA content of 19.2%; and PUFA content of 35.8% by mass. The total recovery of FFA was 86% of the feed mass as determined by hexane extraction of the filtrate.

EXAMPLE 2

Recovery of FFA from Urea Filtrates After Two Crystallisations

This example demonstrates the two-stage concentration of PUFA by sequential urea complexation and supercritical extraction, without intermediate evaporation of ethanol from the FFA.

The FFA obtained from the first separation stage in Example 1 were added to the ethanol/FFA solution obtained as the second separation stage product (minus a small amount used to determine the FFA content and profile). This solution was then mixed with a saturated urea solution as described in Example 1, with a urea to FFA mass ratio of approximately 1:1. The solution, after cooling and then chilling in the freezer overnight, was filtered. 6.35 kg of the filtrate was then pumped at 200 bar, at an average mass flow rate of 1.69 kg per hour. The filtrate was mixed with supercritical $CO_2$ at 200 bar and 40° C. before entering the precipitation chamber. The supercritical carbon dioxide was pumped at the rate of approximately 12.8 kg per hour. A precipitate of mainly ethanol, water, and urea was obtained from the bottom of the precipitation chamber at a rate of approximately 0.15 kg per hour. The supercritical carbon dioxide and dissolved ethanol and FFA passed through two separation stages by sequential pressure reduction as described in Example 1.

The first separation stage yielded an extract containing mainly $C_{20}$-$C_{22}$ PUFA, and some ethanol at an average rate of 0.25 kg per hour. A total of 15 g of FFA were recovered in this fraction after evaporation of the ethanol, with a DHA content of 72%; and PUFA content of 96.3% by mass.

The second separation stage yielded a second extract fraction containing mostly $C_{18}$-$C_{22}$ PUFA and ethanol at an average rate of 1.26 kg per hour. A total of 94 g of FFA was obtained from this fraction (after evaporation of the ethanol from a sample of known mass), with a DHA content of 59%; and PUFA content of 89.4% by mass.

The total recovery of FFA was 95% of the feed mass as determined by hexane extraction of the filtrate.

EXAMPLE 3

Recovery of Urea and FFA from Solids

This example demonstrates the recovery of FFA from urea complexes, and the generation of a dissolved urea fraction that could be recycled for further use. It also demonstrates the separation of AGE from FFA by sequential pressure reduction.

Urea/FFA complex (1210 g) containing spiny dogfish FFA and AGE at a concentration of 23% by mass was dissolved in a mixture containing 2400 g of ethanol and 1600 g of water. The mixture was heated to 40° C. and stirred gently until all of the solid had dissolved. The homogenous liquid phase was then pumped at 200 bar, at a mass flow rate of approximately 1.52 kg per hour, and mixed with supercritical carbon dioxide at 200 bar and 40° C. before entering the precipitation chamber. The supercritical carbon dioxide was pumped at the rate of approximately 12 kg per hour. A precipitate of mainly water and urea was obtained from the bottom of the precipitation chamber at a rate of approximately 0.88 kg per hour. The supercritical carbon dioxide and dissolved ethanol and FFA/AGE passed through two separation stages by sequential pressure reduction as per Example 1.

The first separation stage yielded an extract containing almost exclusively AGE, a small amount of $C_{20}$-$C_{22}$ MUFA, and some ethanol, at an average rate of 0.06 kg per hour. A total of 73 g of AGE and FFA was recovered in this fraction after evaporation of the ethanol.

The second separation stage yielded a second extract fraction containing mostly $C_{14}$-$C_{18}$ SFA and MUFA and ethanol at an average rate of 0.48 kg per hour. No AGE was recovered in this fraction. A total of 194 g of FFA was obtained from this fraction after evaporation of the ethanol.

The total recovery of FFA and AGE was 96% of the feed mass as determined by hexane extraction of the urea complex after dissolution in hot ethanol/water.

EXAMPLE 4

Liquid $CO_2$ Recovery of FAEE from Urea Filtrate

This example describes the recovery of FAEE from a filtrate solution containing ethanol, water, urea and FAEE of Ling liver oil containing 9.3% DHA and 22.5% PUFA.

The filtrate was prepared by dissolving 1.5 kg of urea in ethanol/water (6 L, 90% ethanol) at 65° C. 500 g of FAEE dissolved in ethanol (500 ml) and preheated to 60° C. were added slowly to the urea solution. The mixture was slowly cooled to 4° C. and then vacuum filtered to obtain 6.5 L of filtrate. 151 g of FAEE was retained in the filtrate, and 322 g in the urea solids. 1.206 kg of the filtrate solution was pumped into the apparatus at a rate of 1.2 kg per hour and mixed with liquid $CO_2$ at 298 K and 70 bar. The $CO_2$ was pumped at a rate of 13 kg per hour.

44 g of FAEE were recovered at 97% yield in a single separator-operating at 55 bar and 313 K. The FAEE contained 29% DHA, and 50% PUFA.

EXAMPLE 5

Liquid Propane Recovery of FAEE from Urea Filtrate

This example describes the recovery of FAEE from the same filtrate solution used in Example 4.

2.412 kg of the filtrate solution was pumped into the apparatus, and mixed with subcritical propane at a pressure of 40 bar and temperature of 313 K.

81 g of FAEE at 98% yield was recovered from a single separator operating at a pressure of 9 bar and temperature of 313 K. The FAEE contained 25% DHA and 47% PUFA.

EXAMPLE 6

Supercritical $CO_2$ Recovery of Borage FFA from Urea Filtrate

This example describes the recovery of FFA from a filtrate solution containing ethanol, water, urea and FFA of borage oil containing 22.4% gamma-linolenic acid (GLA), and 60.4% PUFA. The borage oil was obtained by supercritical extraction of borage seed.

Borage oil (401.1 g) was hydrolysed in ethanol/water (1800 ml ethanol, 200 ml water) containing KOH (101.8 g). The mixture was stirred overnight to ensure complete reaction. The solution of hydrolysed borage oil was then neutralised with 6N HCL. The two resultant phases were allowed to separate, and the bottom phase was discarded. A solution of urea was prepared by dissolving 600 g of urea in ethanol/water (2 L, 90% ethanol) at 65° C. The top phase of the hydrolysate solution (preheated to 60° C.) was added to the urea solution, and the mixture cooled to room temperature. The mixture was placed in a freezer overnight at −20° C., and then vacuum filtered to give approximately 4.3 L of filtrate. 238 g of FFA was retained in the filtrate and 144.3 g in the urea solids. 3.629 kg of the filtrate solution was pumped into the apparatus at a rate of 1.1 kg per hour and mixed with supercritical $CO_2$ at 313 K and 200 bar. The $CO_2$ was pumped at a rate of 23.2 kg per hour. The fractionation was carried out with two stage pressure reduction for the recovery of the FFA.

A green coloured raffinate was obtained, which was attributed to chlorophyll.

172 g of FFA containing 35.5% GLA and 89.0% PUFA were recovered in the first separator operating at 100 bar and 323 K.

32 g of FFA containing 36.8% GLA and 88.5% PUFA were recovered in the second separator operating at 48 bar and 313 K.

EXAMPLE 7

Supercritical $CO_2$ Recovery of Winterised Borage FFA from Urea Filtrate with an Additional Water Wash Step This example describes the recovery of FFA from a filtrate solution containing ethanol, water, urea and FFA of borage oil initially containing 23.0% GLA, and 60.8% PUFA in the fatty acid fraction.

The FFA solution was winterised prior to the urea step, to increase the initial GLA content. Two-stage urea fractionation was then carried out, before the supercritical extraction. A high pressure water-wash step was included after the supercritical extraction, and before the first separator, to remove any co-extracted urea before the recovery of the fatty acids. The borage oil was obtained as a waste fraction (minor extract) from the extraction of borage seed with supercritical $CO_2$. The oil contained triglycerides, free fatty acids, and some waxes.

Borage oil (1003.5 g) was hydrolysed in ethanol/water (4500 ml ethanol, 500 ml water) containing KOH (250 g). The mixture was stirred overnight to ensure complete reaction. The solution of hydrolysed borage oil was then neutralised with 6N HCL. The two resultant phases were allowed to separate, and the bottom phase was discarded. The top phase was placed in a freezer overnight, at −20° C. The solution was filtered and the precipitate, which contained 446 g of solids (waxes, saturated fatty acids and salt), discarded. A solution of urea was prepared by dissolving 1.5 kg of urea in ethanol/water (5 L, 90% ethanol) at 65° C. 700 g of FFA containing 26.4% GLA and 70.6% PUFA dissolved in the top phase filtrate (approximately 4 L) and preheated to 60° C. were added slowly to the urea solution. The mixture was slowly cooled to 4° C., then vacuum filtered at 4° C. to obtain approximately 8 L of filtrate. The filtrate was reheated, and further urea added to bring the concentration to the same level as the first urea fractionation. This solution was cooled to −20° C. overnight and then vacuum filtered at 4° C. to give approximately 8 L of solution containing 140.0 g of PUFA. 6.683 kg of the filtrate solution was pumped into the apparatus at a rate of 1.68 kg per hour and mixed with supercritical $CO_2$ at 313 K and 200 bar. The $CO_2$ was pumped at a rate of 24.6 kg per hour.

A green coloured raffinate stream was obtained from the first extraction vessel at a rate of 0.31 kg per hour. The $CO_2$, ethanol and extracted fatty acids passed to a second extraction vessel where the solution was mixed with water pumped at a rate of 0.91 kg per hour. A second raffinate stream was obtained from this extraction vessel at an average rate of 1.20 kg per hour. The fractionation was carried out with two-stage pressure reduction for the recovery of the FFA.

74 g of FFA containing 71.7% GLA and 94% PUFA were recovered in the first separator operating at 100 bar and 323 K.

57 g of FFA containing 75.6% GLA and 96% PUFA were recovered in the second separator operating at 48 bar and 313 K.

EXAMPLE 8

Supercritical $CO_2$ Recovery of FAEE from Urea Filtrate with an Additional Water-Wash Step This example describes the recovery of FAEE from a filtrate solution containing ethanol, water, urea and FAEE of Ling liver oil containing 11.6% DHA, and 21.0% PUFA. A high pressure water-wash step was included after supercritical extraction, and before the first separator, to remove any co-extracted urea. FAEE were prepared according to the methods described above.

A solution of urea was prepared by dissolving 1.5 kg of urea in ethanol/water (6 L, 90% ethanol) at 65° C. 500 g of FAEE dissolved in ethanol (500 ml) and preheated to 60° C. were added slowly to the urea solution. The mixture was slowly cooled to 4° C. and then vacuum filtered to obtain 6.2 L of filtrate. 214 g of FAEE was retained in the filtrate, and 234 g in the urea solids. 5.096 kg of the filtrate solution was pumped into the apparatus at a rate of 1.73 kg per hour and mixed with supercritical $CO_2$ at 315 K and 200 bar. The $CO_2$ was pumped at a rate of 23.2 kg per hour.

A raffinate stream was recovered from the first extraction vessel at an average rate of 0.20 kg per hour. The $CO_2$, ethanol and extracted FAEE passed to a second extraction vessel where the solution was mixed with water pumped at a rate of 0.99 kg per hour. A second raffinate stream was obtained from this extraction vessel at an average rate of 1.34 kg per hour. The fractionation was carried out with two-stage pressure reduction for the recovery of FAEE.

71 g of FAEE containing 31.1% DHA and 54.9% PUFA were recovered in the first separator operating at 100 bar and 323 K.

122 g of FAEE containing 23.1% DHA and 42.46% PUFA were recovered in the second separator operating at 50 bar and 313 K.

Lower molecular mass FAEE were concentrated in the second separator. The extracts from both separators were free from urea.

INDUSTRIAL APPLICATION

It will be appreciated from the discussion above that, in use, the present invention provides a process for extracting polyunsaturated fatty acids, or their derivatives, from crude fats or oils obtained from animal or vegetable sources. The solvents used in the process may be food grade organic solvents and, therefore, the polyunsaturated fatty acids or derivatives are suitable for use as dietary supplements or in the formulation of pharmaceuticals and cosmetics.

The process is particularly suited to the extraction of polyunsaturated fatty acids from fish oils thereby increasing the value of a low to medium value product.

Those persons skilled in the art will further appreciate that the present description is provided by way of example only and that the scope of the invention is not limited to it.

REFERENCES

1. Shahidi, F. "Marine Nutraceuticals" *Inform*, 13, 2002, 57-62
2. Stansby, M. E. "Nutritional Properties of Fish Oil for Human Consumption—Modern Aspects" in Chapter 2 of *Fish Oils in Nutrition*, ed. M. E. Stansby, Van Nostrand Reinhold, New York, 1990

3. Stout, V. F.; Nilsson, W. B.; Krzynowek, J. and Schlenk, H. "Fractionation of Fish Oils and Their Fatty Acids" in Chapter 4 of *Fish Oils in Nutrition,* ed M. E. Stansby, Van Nostrand Reinhold, New York, 1990
4. Hayes, D. G.; Bengtsson, Y. C.; Alstine, J. V. and Setterwall, F. "Urea Complexation for the Rapid, Ecologically Responsible Fractionation of Fatty Acids from Seed Oil" *J. Am. Oil Chem. Soc.* 75, 1998, 1403-1409
5. Catchpole, O. J.; Grey, J. B. and Noermark, K. A. "Solubility of Fish Oil Components in Supercritical $CO_2$ and $CO_2$+ Ethanol Mixtures" *J. Chem. Eng. Data* 43, 1988, 1091-1095
6. Weber, A.; Kümmel, R. and Kraska, T. A. "Closer Look at Gas Antisolvent Crystallisation" *Proceedings of $7^{th}$ Meeting on Supercritical Fluids,* Antibes, France, 2000, Tome 1, 71-76
7. Kulås, E. and Breivik, H. "Recovery of Polyunsaturated Fatty Acids from Urea Adducts" PCT Publication No. WO01/10809
8. Hiroshi, U et al. "Concentration and Separation of Highly Unsaturated Fatty Acid or its Ester" Japanese Patent No. JP60214757
9. Kim, J.-D.; Lim, J.-S. and Lee, Y.-W. "Separation of EPA and DHA from Fatty acid of Fish Oil by Urea adduct Formation using Supercritical Carbon Dioxide Solvent" *J. Korean Oil Chem. Soc.* 14, 1997, 41-48
10. Nillson, W. B.; Gauglitz, E. J.; Hudson, J. K.; Stout, V. F. and Spinelli, J. "Fractionation of Menhaden Oil Ethyl Esters using Supercritical Fluid $CO_2$" *J. Am. Oil Chem. Soc.* 65, 1988, 109-117
11. Nillson, W. B.; Gauglitz, E. J. and Hudson, J. K. "Supercritical Fluid Fractionation of Fish Oil Ethyl Esters using Incremental Pressure Programming and a Temperature Gradient" *J. Am. Oil Chem. Soc.* 66, 1989, 1596-1600
12. Hayes, D. G.; Alstine, J. V. and Asplund, A.-L. "Triangular Phase Diagrams to Predict the Fractionation of Free Fatty Acid mixtures via Urea Complex Formation" *Sep. Sci. Tech.* 36, 2001, 45-58
13. Tomas, F. and Olsson, G. "Process for Separating Lipophilic Compounds" PCT Publication No. WO95/11216 and U.S. Pat. No. 5,734,071
14. Liang, J.-H. and Hwang, L. S. "Fractionation of Squid Visceral Oil Ethyl Esters by Short Path Distillation" *J. Am. Oil Chem. Soc.* 77, 2000, 773-777
15. Luddy, F. E.; Barfold R. A. and Riemenscheider, R. W. "Direct Conversion of Lipid Components to Their Fatty Acid Methyl Esters" *J. Am. Oil Chem. Soc.* 37, 1960, 447-451
16. Malins, D. C.; Wekell J. C. and Houle, C. R. "Composition of the diacyl glyceryl ethers and triglycerides of the flesh and liver of the dogfish (*Squalus acanthias*)" *J. Lipid Res.* 6, 1965, 100-105

The invention claimed is:

1. A process for extracting at least one fatty acid from a lipid hydrolysate solution, which process includes at least the steps of:
    (a) combining the hydrolysate solution with urea to produce a solid urea/lipophilic compound complex;
    (b) separating the solid complex from the solution;
    (c) contacting the solution from step (b) with a near-critical fluid to produce a urea containing precipitate and a near-critical fluid phase containing the fatty acid;
    (d) separating the near-critical fluid phase from the urea containing precipitate; and
    (e) reducing the pressure of the near-critical fluid phase to recover the fatty acid.

2. The process according to claim 1 wherein the lipid hydrolysate solution is obtained from the hydrolysis of fish, animal or plant oil.

3. The process according to claim 2 wherein the oil is fish oil.

4. The process according to claim 2 wherein the oil is seed oil selected from the group consisting of: borage; blackcurrant; evening primrose; Echium; Lunarium; meadowfoam; saw palmetto; pumpkin; and Biota orientalis.

5. The process according to claim 1 wherein the hydrolysate solution is combined with solid urea.

6. The process according to claim 1 wherein the hydrolysate solution is combined with a solution of urea.

7. The process according to claim 1 wherein the fatty acid is unsaturated.

8. The process according to claim 1 wherein the unsaturated fatty acid is polyunsaturated.

9. The process according to claim 1 wherein the polyunsaturated fatty acid is selected from the group consisting of: all cis-5,8,11,14,17-eicosapentaenoic acid; all cis-4,7,10,13,16,19-docosahexaenoic acid; 6,9,12-octadecatrienoic acid; 9,12,15-octadecatrienoic acid; and 9,11-octadecadienoic acid.

10. The process according to claim 1 wherein the lipid hydrolysate solution is a $C_1$-$C_4$ alcohol containing solution.

11. The process according to claim 10 wherein the alcohol is ethanol.

12. The process according to claim 1 wherein the lipid hydrolysate solution is an aqueous alcohol containing solution.

13. The process according to claim 1 wherein the near-critical fluid is selected from the group consisting of: supercritical $CO_2$; liquid $CO_2$; ethane; ethylene; propane; propylene; butane; fluorinated $C_2$-$C_3$ hydrocarbons; nitrous oxide; sulfur hexafluoride; dimethylether; partially and fully fluorinated analogues of dimethylether; and mixtures of any two or more of these gases.

14. The process according to claim 1 wherein the near-critical fluid is supercritical $CO_2$ or liquid $CO_2$.

15. The process according to claim 1 wherein the near-critical fluid is supercritical $CO_2$.

16. The process according to claim 15 wherein the filtrate solution is contacted with supercritical $CO_2$ at a temperature in the range 308-353 K and a pressure in the range 150-500 bar.

17. The process according to claim 16 wherein the pressure is in the range 150-300 bar.

18. The process according to claim 1 wherein the solution and near-critical fluid are contacted using a static mixer.

19. The process according to claim 1 wherein the urea containing precipitate is obtained as an aqueous solution.

20. The process according to claim 1 wherein the pressure of the near-critical fluid phase is reduced in two or more steps to recover two or more fractions containing a fatty acid.

21. The process according to claim 1 wherein the extraction is carried out as a continuous process wherein the urea containing precipitate and the near-critical fluid phase are continuously removed from an extraction vessel without reducing the pressure of the vessel.

22. The process according to claim 1 further including the step of washing the near-critical fluid phase in a high-pressure water wash column before reducing the pressure of the near-critical fluid phase to recover the fatty acid.

23. The process according to claim 1 further comprising extracting a lipophulic compound, said process including at least the steps of:

(f) dissolving the solid urea/lipophilic compound complex in a suitable solvent or solvent mixture to form a solution;

(g) contacting the solution with a near-critical fluid to produce a urea containing precipitate and a near-critical fluid phase containing the lipophilic compound;

(h) separating the near-critical fluid phase from the urea containing precipitate; and (i) reducing the pressure of the near-critical fluid phase to recover the lipophilic compound.

24. The process according to claim 23 wherein the lipophilic compound is selected from the group consisting of: saturated fatty acids; monounsaturated fatty acids; and alkoxyglyceryl ethers.

25. A process for extracting a non-glyceride component from an oil solution, said oil solution comprising an oil dissolved in a suitable solvent or solvent mixture, which process includes at least the steps of:

(a) combining the oil solution with urea to produce a solid urea/lipophilic compound complex;

(b) separating the solid complex from the solution;

(c) contacting the solution from step (b) with a near-critical fluid to produce a urea containing precipitate and a near-critical fluid phase containing the non-glyceride component;

(d) separating the near-critical fluid phase from the urea containing precipitate; and (e) reducing the pressure of the near-critical fluid phase to recover the non-glyceride component.

26. The process according to claim 25 wherein the non-glyceride component is selected from the group consisting of: squalene; vitamin E; and carotenoids.

27. The process according to claim 25 wherein the solvent or solvent mixture is ethanol or aqueous ethanol.

28. The process according to claim 25 wherein the near-critical fluid is selected from the group consisting of: supercritical $CO_2$; liquid $CO_2$; ethane; ethylene; propane; propylene; butane; fluorinated $C_2$-$C_3$ hydrocarbons; nitrous oxide; sulfur hexafluoride; dimethylether; partially and fully fluorinated analogues of dimethylether; and mixtures of any two or more of these gases.

29. The process according to claim 25 wherein the near-critical fluid is supercritical $CO_2$ or liquid $CO_2$.

30. The process according to claim 25 wherein the near-critical fluid is supereritical $CO_2$.

31. The process according to claim 30 wherein the filtrate solution is contacted with supercritical $CO_2$ at a temperature in the range 308-353 K and a pressure in the range 150-500 bar.

32. The process according to claim 31 wherein the pressure is in the range 150-300 bar.

33. The process according to claim 25 wherein the solution and near-critical fluid are contacted using a static mixer.

34. The process according to claim 25 wherein the urea containing precipitate is obtained as an aqueous solution.

35. The process according to claim 25 wherein the pressure of the near-critical fluid phase is reduced in two or more steps to recover two or more fractions containing a non-glyceride component.

36. The process according to claim 25 wherein the extraction is carried out as a continuous process wherein the urea containing precipitate and the near-critical fluid phase are continuously removed from an extraction vessel without reducing the pressure of the vessel.

37. The process according to claim 25 further including the step of washing the near-critical fluid phase in a high-pressure water wash column before reducing the pressure of the near-critical fluid phase to recover the non-glyceride component.

38. The process according to claim 25 further comprising extracting a lipophilic compound, said process including at least the steps of:

(f) dissolving the solid urea/lipophilic compound complex in a suitable solvent or solvent mixture to form a solution;

(g) contacting the solution with a near-critical fluid to produce a urea containing precipitate and a near-critical fluid phase containing the lipophilic compound;

(h) separating the near-critical fluid phase from the urea containing precipitate; and (i) reducing the pressure of the near-critical fluid phase to recover the lipophilic compound.

39. The process according to claim 38 wherein the lipophilic compound is selected from the group consisting of: saturated fatty acids; monounsaturated fatty acids; and alkoxyglyceryl ethers.

* * * * *